United States Patent
Huennekens et al.

(10) Patent No.: US 8,797,155 B2
(45) Date of Patent: Aug. 5, 2014

(54) DISTRIBUTED MEDICAL SENSING SYSTEM AND METHOD

(71) Applicant: Volcano Corporation, San Diego, CA (US)

(72) Inventors: R. Scott Huennekens, San Diego, CA (US); David M. Sheehan, Poway, CA (US); Jason Spencer, Rocklin, CA (US); Rex Kerr, Folsom, CA (US); Bill Clark, Davis, CA (US); Richard E. Mansker, Sacramento, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/624,480

(22) Filed: Sep. 21, 2012

(65) Prior Publication Data

US 2013/0015975 A1 Jan. 17, 2013

Related U.S. Application Data

(63) Continuation of application No. PCT/US2012/032343, filed on Apr. 5, 2012.

(60) Provisional application No. 61/473,591, filed on Apr. 8, 2011.

(51) Int. Cl.
  *G08B 1/08* (2006.01)

(52) U.S. Cl.
  USPC .............. 340/539.12; 340/539.11; 340/573.1; 340/539.1; 340/539.17; 340/539.25; 600/300; 600/407; 600/437

(58) Field of Classification Search
  USPC .................... 340/539.1–539.12, 573.3–573.4; 600/300, 407, 437
  See application file for complete search history.

(56) References Cited

U.S. PATENT DOCUMENTS

| | | | |
|---|---|---|---|
| 5,010,890 A | 4/1991 | Pfohl et al. | |
| 5,987,519 A * | 11/1999 | Peifer et al. | 709/230 |
| 6,364,834 B1 * | 4/2002 | Reuss et al. | 600/300 |
| 6,544,174 B2 * | 4/2003 | West et al. | 600/300 |
| 6,694,180 B1 | 2/2004 | Boesen | 600/547 |
| 6,870,484 B1 * | 3/2005 | Brinsfield et al. | 340/8.1 |
| 6,956,572 B2 * | 10/2005 | Zaleski | 345/440.2 |
| 8,289,284 B2 * | 10/2012 | Glynn et al. | 345/173 |
| 2006/0220839 A1 | 10/2006 | Fifolt et al. | |
| 2006/0287586 A1 * | 12/2006 | Murphy | 600/300 |
| 2007/0232933 A1 | 10/2007 | Gille et al. | |
| 2008/0045809 A1 | 2/2008 | Hermannsson | |
| 2009/0273467 A1 * | 11/2009 | Elixmann et al. | 340/539.12 |
| 2011/0001605 A1 * | 1/2011 | Kiani et al. | 340/5.6 |
| 2011/0105854 A1 * | 5/2011 | Kiani et al. | 600/300 |

OTHER PUBLICATIONS

Korean Intellectual Property Office, Notification of Transmittal of the International Search Report and the Written Opinion of the International Searching Authority, or the Declaration for International Application No. PCT/US2012/032343, mailed Oct. 31, 2012, 21 pages.

* cited by examiner

*Primary Examiner* — Daniel Wu
*Assistant Examiner* — Son M Tang
(74) *Attorney, Agent, or Firm* — Haynes and Boone, LLP

(57) ABSTRACT

A method of communicating medical sensing data including receiving, at a patient communication system, medical sensing data collected by a medical sensing device during a medical sensing procedure. The method also includes creating, with the patient communication system, a data message, the data message including at least a portion of the medical sensing data, information about the medical sensing procedure, and information about the medical sensing data and transmitting, with the patient communication system, the data message to a centralized computing device over a data network.

18 Claims, 6 Drawing Sheets

DISTRIBUTED MEDICAL SENSING SYSTEM AND METHOD

CROSS-REFERENCE TO RELATED APPLICATIONS

This application is a continuation of PCT Patent Application No. PCT/US12/32343 filed on Apr. 5, 2012, entitled "DISTRIBUTED MEDICAL SENSING SYSTEM AND METHOD," which claims the benefit of U.S. Provisional Application No. 61/473,591 filed on Apr. 8, 2011 and incorporated by reference herein. The present application claims the benefit of each of the foregoing applications.

TECHNICAL FIELD

Embodiments of the present disclosure relate generally to the field of medical devices and, more particularly, to sensing and imaging systems and associated methods of use.

BACKGROUND

This application is a continuation of PCT Patent Application No. PCT/U.S.12/32343 filed on Apr. 5, 2012, entitled "DISTRIBUTED MEDICAL SENSING SYSTEM AND METHOD," which claims the benefit of U.S. Provisional Application No. 61/473,591 filed on Apr. 8, 2011 and incorporated by reference herein. The present application claims the benefit of each of the foregoing applications.

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy. Each of these techniques may be better suited for different diagnostic situations. To increase the chance of successful treatment, health care facilities may have a multitude of imaging and sensing modalities on hand in a catheter lab during a procedure. However, each imaging modality in a catheter lab traditionally requires its own special-purpose diagnostic equipment. For instance, an imaging modality may require a catheter, a patient isolation module (PIM), a user control interface, a display, a specialized power unit, and a processing unit such as a customized personal computer. Traditionally, all of this equipment is located in the catheter room itself during a procedure and depends on a substantial wiring infrastructure for network connectivity and dependable power. Physical space is typically at a premium in catheter labs and each additional imaging modality employed in a catheter lab complicates the pre-procedure setup and limits the movement of health care professionals during procedures. Additionally, known problems arise when attempting to locate portions of a diagnostic system outside of a catheter lab. For instance, data transmitted between a PIM and a processing unit may degrade as the distance between the two increases. Similarly, traditional long-distance communication links do not support the bandwidth required for modern cardiovascular imaging techniques.

While the existing devices and methods have been generally adequate for their intended purposes, they have not been entirely satisfactory in all respects. The medical sensing systems and associated methods of the present disclosure overcome one or more of the shortcomings of the prior art.

SUMMARY

In one exemplary aspect, the present disclosure is directed to a method of communicating medical sensing data including receiving, at a patient communication system, medical sensing data collected by a medical sensing device during a medical sensing procedure. The method also includes creating, with the patient communication system, a data message, the data message including at least a portion of the medical sensing data, information about the medical sensing procedure, and information about the medical sensing data and transmitting, with the patient communication system, the data message to a centralized computing device over a data network.

In another exemplary aspect, the present disclosure is directed to a distributed medical sensing system. The system includes a computer communication network, a first patient communication system communicatively coupled to a first medical sensor device and the computer communication network, the first patient communication system being operable to transmit, over the computer communication network, a first plurality of packets containing first medical data collected from a first patient by the first medical sensor device and also containing first patient information, and a second patient communication system communicatively coupled to a second medical sensor device and the computer communication network, the second patient communication system being operable to send over the computer communication network a second plurality of packets containing second medical data collected from a second patient by the second medical sensor device and also containing second patient information. The system also includes a centralized computing device communicatively coupled to the computer communication network and operable to receive first and second plurality of packets and operable to respectively process the first medical data based on the first patient information and process the second medical data based on the second patient information.

In yet another exemplary aspect, the present disclosure is directed to a method of processing medical data. The method includes receiving, at a centralized computing device, first message data over a computer communication network, the first message data including first medical sensing data generated by a first medical sensor device during a first medical sensing procedure, information about the first medical sensing procedure, and information about the first medical sensing data. The method also includes processing, with the centralized computing device, the first medical data based on the information about the first medical sensing procedure and the information about the first medical sensing data and transmitting, with the centralized computing device, second message data to a first user interface device over the computer communication network, the second message data containing the first medical data in processed form, the first user interface device being operable to display the first medical data in processed form.

BRIEF DESCRIPTION OF THE DRAWINGS

FIG. 4 is an illustration of a message format utilized by the distributed medical sensing system of FIG. 1 in one embodiment of the present disclosure.

FIG. 5 is an illustration of a different message format utilized by the distributed medical sensing system of FIG. 1 in another embodiment of the present disclosure.

DETAILED DESCRIPTION

Figure 1:
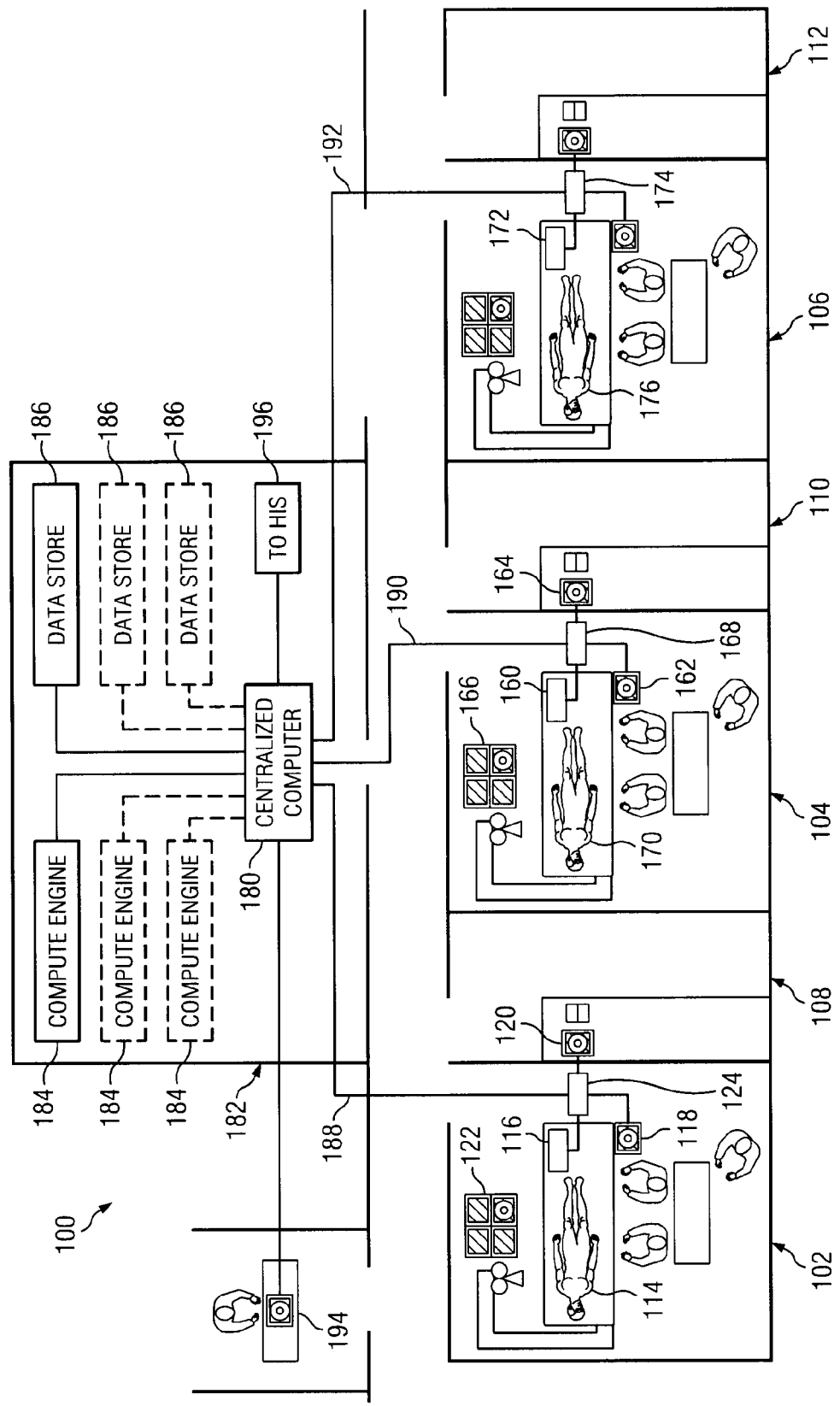
FIG. 1 is a schematic drawing depicting a distributed medical sensing system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

FIG. 1 is a schematic drawing depicting a distributed medical sensing system 100 according to one embodiment of the present disclosure. The distributed medical sensing system 100 is a network-based distributed computational and storage solution for multiple modality medical sensing. Generally, in the medical sensing system 100, medical data is collected by network-connected sensing instruments in catheter labs but processed and stored in a centralized location and returned to the catheter labs for display to and analysis by health care professionals.

In the present embodiment, the medical sensing system 100 is implemented in a health care facility with catheter labs 102, 104, and 106. As illustrated in FIG. 1, each catheter lab 102, 104, and 106 has an associated control room 108, 110, and 112. The catheter labs 102, 104, and 106 are sterile but their associated control rooms 108, 110, and 112 may or may not be sterile depending on the requirements of a procedure and/or health care facility. Each catheter lab/control room pair may be used to perform on a patient any number of medical sensing procedures such as angiography, intravascular ultrasound (IVUS), forward looking IVUS (FL-IVUS), a fractional flow reserve (FFR) determination, a coronary flow reserve (CFR) determination, optical coherence tomography (OCT), computed tomography, intracardiac echocardiography (ICE), intravascular palpography, transesophageal ultrasound, or any other medical imaging modalities known in the art. For example, in catheter lab 102 a patient 114 may be undergoing an IVUS procedure, in which a phased-array catheter (not illustrated) is inserted into the patient's arteries.

The medical sensing system 100 includes a number of interconnected diagnostic tools in the catheter lab 102 and control room 108 to facilitate this procedure, including a patient isolation module (PIM) 116, a bedside control surface 118, a control room control surface 120, and a boom display 122. The medical sensing system 100 further includes a bedside utility box (BUB) 124 in the catheter lab 102 to interconnect these diagnostic tools and to connect to system 100. That is, the BUB 124 is a central hub to which the diagnostic tools in the catheter lab 102 and control room 108 connect to the network-based system 100. In one embodiment, each of the PIM 116, bedside control surface 118, and control room control surface 120 connect to the BUB 124 with similar standardized connectors and communicate with the BUB 124 using a standardized protocol. The BUB 124 will be described in greater detail in association with FIG. 2.

Although the BUB 124 is shown as a unit for connecting multiple diagnostic devices to the system 100, it is contemplated that in a further embodiment each diagnostic device may include a communication module that can directly access the system 100 and communicate with one or more other devices connected to the network of system 100. Such communication modules include processors and/or logic to send addressed messages over the network and receive addresses messages from the network. In one aspect the network may utilize the TCP/IP protocol for network communication. Such network communications may be made over a wired connection or over a wireless connection.

In the illustrated embodiment, the BUB 124 is communicatively coupled to the patient isolation module (PIM) 116, which is, in turn, coupled to a sensor device (not-illustrated) that collects medical data from a patient. In general, the PIM 116 is a patient communication system that acts as an intermediary between the medical sensing system 100 and data collection sensors. In some embodiments, the PIM and the BUB together may be considered a patient communication system. In the above example of IVUS, the PIM 116 is the intermediary between the BUB 124 and a phased-array catheter. For convenience purposes, the PIM 116 may hang from the patient table or may be placed in another location near the patient. The PIM 116 provides power to the phased-array catheter by way of its connection to the BUB 124. Typically, different sensory instruments require different amounts of power, and thus their associated PIMs may draw different amounts of power from the BUB 124. The PIM 116 further transmits data collected with the catheter to the BUB 124. In one embodiment, the PIM 116 includes an analog to digital (A/D) converter and transmits digital data to the BUB 124, however, in other embodiments the PIM transmits analog data to the BUB. Further, in some embodiments, the PIM 116 and BUB 124 communicate with a standardized data transmission protocol, such as Synchronous Optical Networking (SONET). In the illustrated embodiment, the PIM 116 and BUB 124 communicate over a wired connection such as a standard copper link or a fiber optic link but, alternatively, the PIM 116 and BUB 124 may wirelessly communicate. Although only one PIM is depicted as connected to the BUB 124, additional PIMs associated with different medical sensing modalities may be connected to BUB 124. Any such additional PIMs may communicate with the BUB 124 concurrently with the PIM 116. Additionally, in some embodiments, such as those in which patient data is collected using angiography, the illustrated PIM may be replaced with a C-arm. In such embodiments, the C-arm may act as the power and data intermediary between the actual data collection tools and the system 100. U.S. Patent Application Publication No. U.S. 2007/0232933, entitled "Component-Based Catheter Lab Intravascular Ultrasound System," discloses a component-based IVUS system that includes a PIM and is hereby incorporated by reference in its entirety.

The bedside control surface 118 is also communicatively coupled to the BUB 124 and provides user control of the particular medical sensing modality (or modalities) being used to diagnose the patient 114. In the current embodiment, the bedside control surface 118 is a touch screen that provides user controls and diagnostic images on a single surface. In alternative embodiments, however, the bedside control surface 118 may include both a non-interactive display and separate controls such as physical buttons and/or a joystick. In the illustrated embodiment, the bedside control surface 118 and BUB 124 communicate over a wired connection such as a standard copper link or a fiber optic link but, alternatively, the control surface 118 and BUB 124 may wirelessly communicate. Further, in some embodiments, the bedside control surface 118 may be also communicatively coupled directly to the PIM 116. The bedside control surface 118 includes an integrated processing unit to drive a graphical user interface (GUI)-based workflow presented on the touch screen. In an exemplary embodiment, the particular GUI-based workflow presented by the bedside control surface 118 depends on the medical sensing modality being used to diagnose the patient 114. To this end, the bedside control surface 118 is capable of displaying multiple GUI-based workflows, each corresponding to a particular sensor or imaging modality or simultaneous combination thereof. A software framework executing on the bedside control surface 118 manages the multiple workflows. This software framework will be discussed in greater detail in association with FIG. 3. Further, in some embodiments, the bedside control surface 118 automatically displays an appropriate workflow based on the particular PIM connected to the BUB 124. In the event that multiple PIMs are coupled to BUB 124, the bedside control surface 118 may present a user with a modality selector screen on which the appropriate GUI-based workflow may be selected. U.S. Pat. No. 7,134,994, entitled "Multipurpose Host System For Invasive Cardiovascular Diagnostic Measurement Acquisition and Display," discloses a multifunction diagnostic system with a multi-mode graphical user interface and is hereby incorporated by reference in its entirety. U.S. Patent Application Publication No. U.S. 2008/0269572, entitled "Multipurpose Host System For Invasive Cardiovascular Diagnostic Measurement Acquisition Including An Enhanced Dynamically Configured Graphical Display," discloses a method for dynamically switching between cardiovascular diagnostic GUIs and is also hereby incorporated by reference in its entirety.

The control room control surface 120 in the control room 108 is also communicatively coupled to the BUB 124 and, as shown in FIG. 1, is adjacent to catheter lab 102. In the illustrated embodiment, the control room control surface 120 and BUB 124 communicate over a wired connection such as a standard copper link or a fiber optic link but, alternatively, the control surface 120 and BUB 124 may wirelessly communicate. In the current embodiment, the control room control surface 120 is similar to the bedside control surface 118 in that it includes a touch screen, integrated processing unit, and multitude of GUI-based workflows corresponding to different medical sensing modalities. During a procedure, however, the control room control surface 120 may be used to carry out a different aspect of the procedure's workflow than the bedside control surface 118. In alternative embodiments, the control room control surface 120 may include a non-interactive display and standalone controls such as a mouse and keyboard. Further, the processing unit of the control room control surface 120 may be more powerful than the processing unit of the bedside control surface 118. In one embodiment, the control room control surface 120 may drive the boom display 122. The boom display 122 may include an array of monitors, each capable of displaying different information associated with a medical sensing procedure. For example, during an IVUS procedure, one monitor in the boom display 122 may display a tomographic view and one monitor may display a sagittal view. In alternative embodiments, the boom display 122 may be coupled directly to and driven by the BUB 124, the bedside control surface 118, or another network-connected device.

Figure 2:
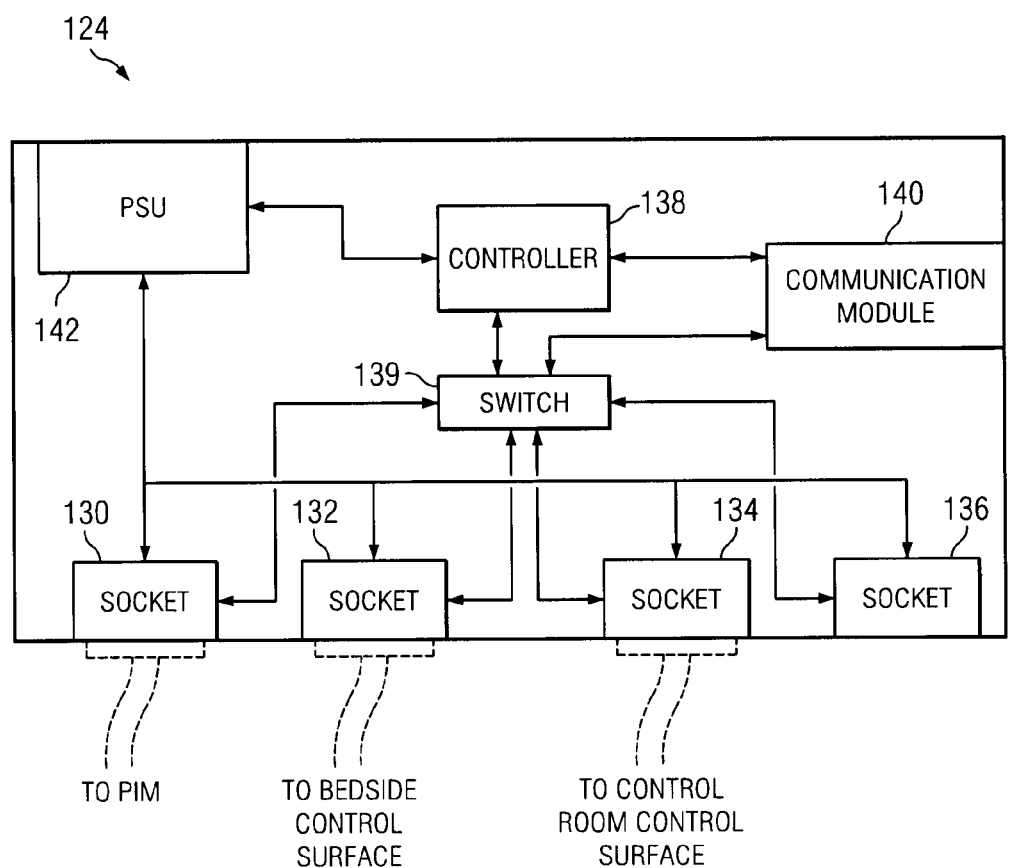
FIG. 2 is a functional block diagram of an exemplary embodiment of an aspect of the distributed medical sensing system of FIG. 1, specifically, a bedside utility box.

With reference now to FIG. 2, the BUB 124 is described in greater detail. FIG. 2 is a functional block diagram of an exemplary embodiment of the BUB 124. The BUB 124 includes connector sockets 130, 132, 134, and 136. In one embodiment, the sockets 130, 132, 134, and 136 may be substantially similar (i.e. standardized), but in other embodiments, each socket may be a dedicated socket specifically configured to cooperate with a specific medical sensing system. As illustrated, the BUB 124 includes four connector sockets, but alternatively it may include a greater number or fewer number of sockets. Diagnostic tools such as medical sensing devices and user interfaces may connect to the sockets and become part of the network-based system 100. For example, PIM 116 may connect to socket 130, bedside control surface 118 may connect to socket 132, and control room control surface 120 may connect to socket 134. Upon connection of a diagnostic tool to a socket, the BUB 124 provides data connectivity and power to that diagnostic tool. In the current embodiment, diagnostic tools such as PIM 116 are communicatively coupled to the BUB 124 via a wired connection, but, alternatively, data transfer may be accomplished over a fiber optic link or wireless connection. In the latter case, the sockets 130, 132, 134, and 136 may be replaced with a multi-connection wireless communication module.

The BUB 124 further includes a controller 138, a switch 139, and a communication module 140. In one some embodiments, the controller 138 may be a low-power microcontroller with integrated memory and peripherals. The controller 138 is operable, among other things, to route data from the sockets 130, 132, 134, and 136 to the communication module 140 via the switch 139. The switch 139 may be a hardware-based switch or may be a software-based switch integrated into the communication module 140. In the current embodiment, the controller 138 includes an analog to digital (A/D) converter which the controller may selectively utilize based on whether data incoming from a connected PIM is analog or digital. For example, the controller 138 may convert analog data from a PIM to digital data before it is routed to the communication module. Additionally, in some embodiments, the controller 138 may be operable to associate identifying information with the medical sensing data when it is digitized. More specifically, the controller 138 may create a plurality of messages from the incoming analog data stream, where each message contains a portion of the digitized medical sensing data and a header. The contents of these messages will be described in more detail in association with FIGS. 4 and 5. Further, in some embodiments where the PIMs digitize the sensing data before transmitting it to the BUBs, the PIMs themselves may be operable to create these messages.

Further, in the event that multiple medical sensing devices are coupled to the BUB 124, the controller 138 may be operable to facilitate time synchronization among the devices for co-registration purposes. For instance, in one embodiment, the controller 138 may be operable to serve as a master time server for the downstream sensing devices using a network-based time synchronization protocol such as the Precision Time Protocol (PTP) or the Network Time Protocol (NTP). In another embodiment, the controller 138 may be operable to assign a common timestamp to data as it arrives into the BUB 124 from a plurality of medical sensing devices. Further, in another embodiment, the controller 138 may communicate with connected medical sensing devices using a synchronous protocol such as Synchronous Optical Networking (SONET), and may assign timestamps to incoming medical sensing data based on the multiplexed communication. Still further, in other embodiments, the BUB 124 may include a dedicated real-time clock to synchronize sampling by connected medical sensing devices. In such an embodiment, the real-time clock may distribute a synchronization signal to connected sensing devices and also the controller 138 which may act as a co-registration processor. In some embodiments, the real-time clock may be integrated into the controller 138.

Further, in some embodiments, the controller 138 may be operable to modify the medical data received from the medical sensing devices before it is routed to the communication module 140. For example, in some embodiments, the controller 138 may compress the data before it is transmitted over the network-based system 100. In this manner, large data sets produced by imaging modalities such as OCT may be more efficiently moved over system 100. In some embodiment, the controller 138 may also be operable to filter incoming sensing data in some manner. As mentioned above, PIMs in system 100 may communicate directly with the system 100 without the use of BUBs, in which case, and compression and/or filtering of medical data may take place in the PIMs themselves rather than in the BUBs.

The communication module 140 in the BUB 124 is a high-speed communication port operable to transmit data between the diagnostic tools connected to the BUB 124 and the distributed medical sensing system 100. In embodiments in which the system 100 includes a packet-based network, the communication module 140 is operable to packetize medical sensing data routed through (and possibly digitized by) the controller 138, address the resulting packets, and the send the packets out over the system 100. In the embodiments in which the controller 138 segments incoming sensing data into messages, the communication module 140 may encapsulate the messages into TCP/IP packets for transmission over the network-based system 100. In the illustrated embodiment, the communication module 140 is an InfiniBand switched fabric communications module, however, in other embodiments the communications module may be a HyperTransport communication module, a fiber optic link module, a Gigabit Ethernet module, a high-speed wireless module or some other high-speed link module known in the art. Still further, in some embodiments, the above A/D conversion and packetizing/addressing/sending functionality of the BUB 124 may be instead embedded into a PIM, thereby negating the necessity of a BUB.

The BUB 124 further includes a medical-grade power supply unit (PSU) 142. The PSU 142 provides power to the controller 138 and the diagnostic tools (e.g. medical sensing devices, control surfaces) connected to the sockets 130, 132, 134, and 136. Note that the block diagram shown in FIG. 2 has been simplified for the sake of clarity. A person of ordinary skill in the art would understand that elements of the BUB 124 may be rearranged or combined and that additional elements may be added without changing the functionality described herein. U.S. Provisional Patent Application No. 61/473,625, entitled "MEDICAL SENSING COMMUNICATION SYSTEM AND METHOD" and filed on Apr. 8, 2011, discloses a bedside utility box that intelligently couples medical sensing-related tools and is hereby incorporated by reference in its entirety.

With reference back to FIG. 1, the distributed medical sensing system 100 includes a second set of diagnostic tools in the catheter lab 104 and associated control room 110, including a PIM 160, a bedside control surface 162, a control room control surface 164, and a boom display 166. A BUB 168 interconnects the diagnostic tools in the catheter lab 104 and control room 110 and may be similar to the BUB 124. Like catheter lab 102, catheter lab 104 supports any number of medical sensing modalities. For instance, a patient 170 may be undergoing an OCT procedure, in which an OCT catheter (not illustrated) is inserted into the patient's arteries. The OCT catheter is coupled to the PIM 160, which in turn is coupled to the BUB 168. Similarly, the bedside control surface 162 and control room control surface 164 are also connected to the BUB 168.

Further, the distributed medical sensing system 100 includes an additional set of diagnostic tools in the catheter lab 106 and associated control room 112, including a PIM 172 coupled to a BUB 174. Here, a patient 176 may be undergoing yet another procedure, for example, a FFR procedure, in which a pressure sensor at the distal end of a guide wire or catheter is inserted into the patient's body.

The distributed medical sensing system 100 further includes a centralized computer 180 that is operable to manage system resources in the network and also to process medical data collected in catheter labs 102, 104, and 106. In the illustrated embodiment, the centralized computer 180 is a single server-type computer, but, in other embodiments, centralized computer may be multiple interconnected computers. A software framework executing on the centralized computer 180 manages the processing of medical data transmitted from the catheter labs. This software framework will be discussed in greater detail in association with FIG. 3. In the current embodiment, the centralized computer 180 is located in a server room 182 in the same health care facility as the catheter labs and, as such, may be separated by tens to hundreds of meters from the catheter labs depending on the size of the health care facility. However, in other embodiments the centralized computer 180 may be located outside of the health care facility many kilometers away, as discussed later in association with FIG. 7. Further, the processing power of the centralized computer 180 is scalable depending on the needs of the health care facility. To this end, as illustrated in FIG. 1, the medical sensing system 100 includes an array of compute engines 184 communicatively coupled to the centralized computer 180 in the server room 182. The number of compute engines in the array 184 may be increased or decreased according to processing needs. For example, a health care facility that transitions from performing mostly low processor intensive procedures, such as FFR, to performing mostly processor intensive procedures, such as OCT, may add additional compute engines to the array 184, thereby increasing the processing power of the centralized computer 180. In the current embodiment, the compute engines in the array 184 are server-type computers clustered together in a high-speed network, however, the compute engines may alternatively be networked processors in a massively parallel processor implementation. Further, in other embodiments, the compute engine array may be implemented with general-purpose computing on graphics processing units (GPGPUs). In such a scenario, each compute engine may be an add-in card with an array of graphics processing units (GPUs) such as a Tesla GPGPU card available from Nvidia Corporation of Santa Clara, Calif. When diagnostic data is transmitted to the centralized computer 180 from the catheter labs, the computer is operable to process the data in a parallel manner using the compute engine array 184. U.S. Patent Application Publication No. U.S. 2009/0093980, entitled "Real Time SD-OCT With Distributed Acquisition and Processing," discloses a system for processing medical data in parallel and is hereby incorporated by reference in its entirety. And U.S. patent application Ser. No. 12/978,344, entitled "Integrated System Architectures and Methods of Use," discloses an integrated system for collecting and processing medical data and is hereby incorporated by reference in its entirety.

The diagnostic system 100 further includes a storage array 186 coupled to the centralized computer 180. In one embodiment, the storage array 186 is configured to store patient data in a manner conforming to Digital Imaging and Communications in Medicine (DICOM) standards. For example, the storage array 186 may archive patient images collected by the various medical sensing modalities in the catheter labs 102, 104, and 106. Like the compute engine array 184, the storage array 186 is scalable to meet the needs of the health care facility. In the current embodiment, the storage array 186 is a storage area network of interconnected storage devices, but alternatively it may be an array of hard disks in the centralized computer 180, an array of tape drives, or some other scalable storage solution.

The BUBs 124, 168, and 174 are communicatively coupled to the centralized computer 180 by communication interconnects 188, 190, and 192. In the current embodiment, the communication interconnects are InfiniBand links but alternatively may be another type of high-speed interconnect such as HyperTransport links, or may be high-speed wireless communication interconnects. The BUBs 124, 168, and 174, centralized computer 180, and other network devices in the diagnostic system 100 may communicate over the communication interconnects using a secure protocol, such as Transport Layer Security (TLS) over TCP/IP. Additionally, to help facilitate co-registration of multi-modality sensing data the BUBs 124, 168, and 174 may communicate with the centralized computer 180 using a synchronized protocol such as SONET. Further, to reduce wiring clutter in the catheter labs, the interconnects 188, 190, and 192 may extend toward their respective catheter lab underneath the floor in a cable trench and break out of the floor in the labs through cabling ports near their respective BUBs 118, 168, and 174, and make a single connection to the BUBs.

Further, a doctor or other health professional may access the medical sensing system 100 through a networked computing device 194. The computing device 194 may access patient information stored on the storage array 186, or, in some embodiments, monitor one or more on-going procedures in the catheter labs in real time. The computing device 194 may access the system 100 through a wired or wireless network connection using a known communication protocol such as Ethernet or IEEE 802.11. In some embodiments a network bridge may be required to interconnect a standard Ethernet-based network and a high-speed network, such as the above-described InfiniBand network. In the current embodiment, the computing device 194 is a laptop used by a doctor in a doctor's office, but in other embodiments the computing device may be a PC, smartphone, tablet computer, or other device with a network connection located inside or outside of the health care facility. Additionally, the medical sensing system 100 may be communicatively coupled to a hospital information system (HIS) 196 that manages the administrative, financial and clinical aspects of the health care facility, and also communicatively coupled to a picture archive and communication system (PACS) of the health care facility. In some embodiments, the centralized computer 180 may be operable to request patient workflow data from DICOM servers on the HIS 196. For instance, the centralized computer 180 may use the DICOM patient data to schedule procedures in the catheter labs and also customize workflows for particular patients. The connections to the HIS 196 and PACS may be implemented using a network bridge or some other networking device.

Figure 3:
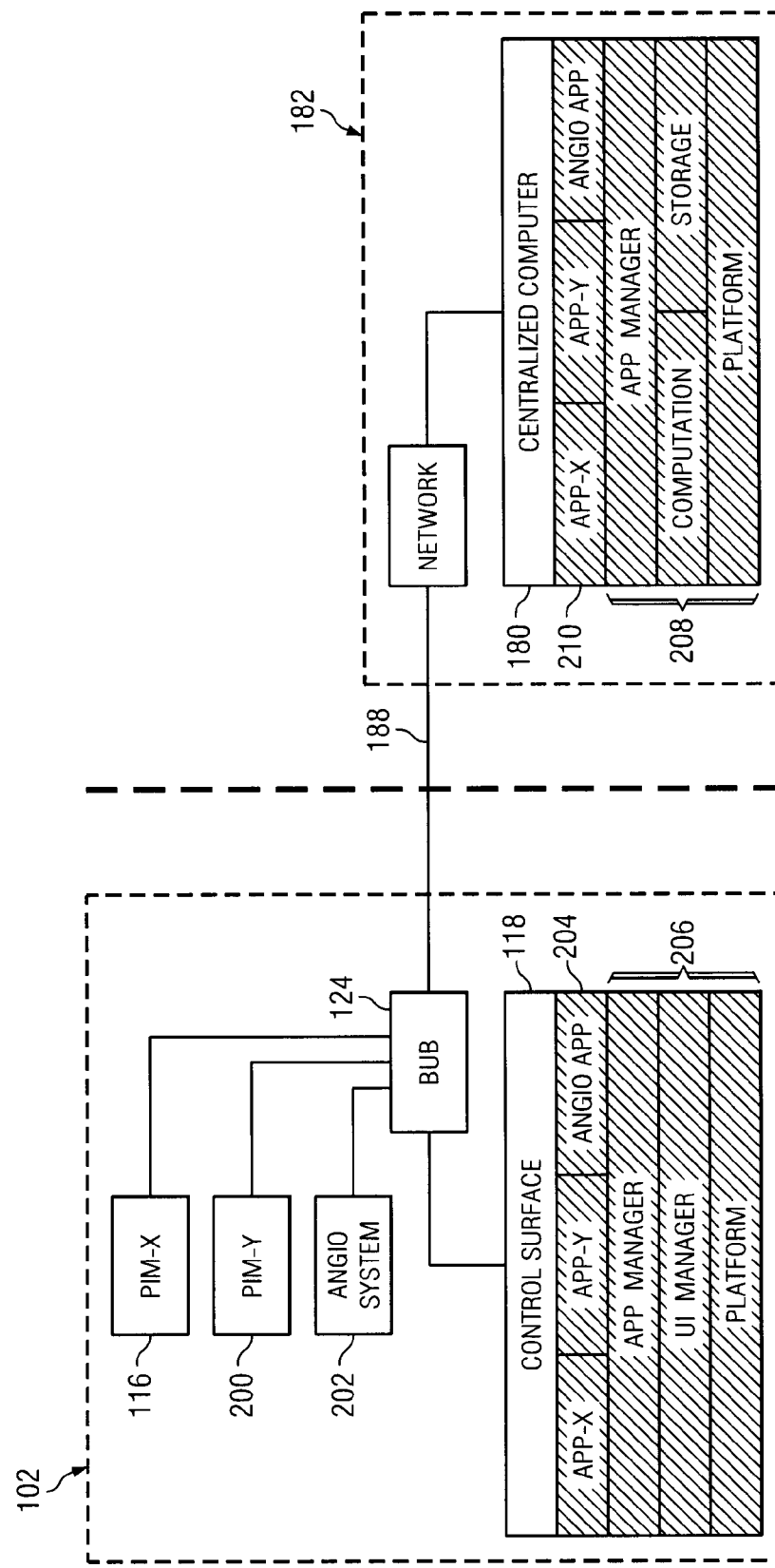
FIG. 3 is a functional block diagram of another aspect of the distributed medical sensing system of FIG. 1 that includes a software framework executing on a bedside control surface and a software framework executing on a centralized computer.

With reference now to FIG. 3, the software frameworks executing in the distributed medical sensing system 100 are described in greater detail. FIG. 3 is a functional block diagram of a portion of the system 100, including the software framework executing on the bedside control surface 118 and the software framework executing on the centralized computer 180. The left portion of FIG. 3 illustrates one configuration of catheter lab 102, in which two PIMSs, an angiography system, and the bedside control surface 118 are connected to BUB 124. Specifically, the PIM 116, a PIM 200, and an angiography system 202 are connected to the BUB 124. In the current embodiment, the PIMs 116 and 200 and angiography system 202 are used for different medical sensing modalities, and thus the associated workflows are different. However, in the exemplary embodiment, a health care professional may control all three medical sensing workflows from the bedside control surface 118. In more detail, the bedside control surface 118 includes a software framework in which user interface (UI) applications for each medical sensing modality may execute within a UI application layer 204. The software framework also includes a software stack 206 that executes underneath and supports the layer of UI applications 204. In the current embodiment, the software stack 206 exposes a set of application programming interfaces (APIs) with which the applications in the UI application layer 206 may call to access system resources such as a look-and-feel toolbox and communication infrastructure.

Using components of the look-and-feel toolbox, each UI application 204 may present a GUI that gives a user control over an imaging or signaling modality workflow and also presents imaging or signaling data collected from the associated PIM and processed by the centralized computer 180. Further, co-registration UI applications may present and/or combine processed image or signaling data from multiple modalities. For instance, a UI application may display an electrocardiogram (ECG) wave adjacent to IVUS imaging data or may display an IVUS image overlaid with borders that were previously drawn on an OCT image. Such co-registration UI applications may harness the parallel processing power of the centralized computer 180 and acquire data from two medical data streams simultaneously to facilitate a real time co-registration workflow. In an exemplary embodiment, additional UI applications may be added to the application layer 204 to support new medical sensing modalities or co-registration techniques developed after the control surface 118 has been deployed. Further, the API-based software framework allows the UI applications 204 to be independent of the software stack 206 and thus written by third parties to control a custom workflow. As mentioned above, in some embodiments, the bedside control surface 118 may automatically select the appropriate UI application (and thus the appropriate workflow) based on the particular PIM connected to the BUB 124. In the event that multiple PIMs are coupled to BUB 124, as is illustrated in FIG. 3, the bedside control surface 118 may present a user with a modality selector screen on which the desired GUI may be selected.

As described in association with FIG. 1, the BUB 124 is communicatively coupled to the centralized computer 180 via the communication interconnect 188. Like the bedside control surface 118, the centralized computer 180 includes an API-based software framework in which processing applications associated with medical sensing modalities may execute. In particular, the centralized computer 180 includes a software stack 208 that executes underneath and supports a layer of processing applications 210. Processing applications in the application layer 210 may correspond to a medical sensing modality in use in the health care facility and processes all data for that particular sensing modality. For example, every PIM in the health care facility that collects IVUS data may send the data over the system 100 to an IVUS processing application in the application layer 210 on centralized computer 180. The IVUS processing application may interpret the IVUS data and send image data back over the system 100 to IVUS UI applications on the bedside control surfaces for display. Further, in some embodiments, the application layer 210 may include co-registration applications, in which medical sensing data from a plurality of medical sensing devices are co-registered and returned to co-registration UI applications on control surfaces. To support such co-registration applications, in one embodiment, the software stack 208 may expose one or more time synchronization APIs for use by the applications. For instance, the centralized computer 180 may act as a master clock using the NTP or PTP protocols where each BUB in the system 100 is a client or, alternatively, the computer 180 may include a dedicated real-time clock. In either case, co-registration applications in the application layer 210 may have access to synchronization data via APIs exposed by the software stack 208. U.S. Provisional Patent Application No. 61/473,570, entitled "MULTI-MODALITY MEDICAL SENSING SYSTEM AND METHOD" and filed on Apr. 8, 2011, discloses a computing resource with a similar modular API-based software framework capable of processing multi-modality medical sensing data and is hereby incorporated by reference in its entirety.

The software stack 208 executing on the centralized computer 180 is operable to utilize the parallel processing power of the compute engine array 184. As such, the processing applications 210 can process signaling and imaging data from multiple on-going procedures concurrently. In this regard, in some embodiments, the software stack 208 may intelligently make use of the computing resources available to centralized computer 180 by identifying generic computing tasks common to concurrently executing processing applications. For example, the software stack 208 may determine that two processing applications (associated with different modalities) each need to perform filtering, image processing, and scan conversion processes on incoming sensing data. Once these common tasks are identified, the software stack 208 may utilize a library of parallel algorithms to process these tasks concurrently.

Further, after processing medical sensing data for a procedure, the processing applications 210 may store the data in the storage array 186. Additionally, the processing applications 210 may manage the workflows for the associated UI applications installed on the control surfaces. In an exemplary embodiment, additional processing applications may be added to the application layer 210 to support new medical sensing modalities and new UI applications on the control surfaces. For example, to support a new medical sensing modality, a third party may develop a new catheter-based sensor, new PIM, new UI application, and new processing application. In such a scenario, the new PIM may connect to BUB 124, the new UI application may be installed onto the existing control surface 118 and call the APIs exposed by the software stack 206, and the new processing application may be installed onto the centralized computer 180 and call the APIs exposed by the software stack 208.

Figures 4, 5:
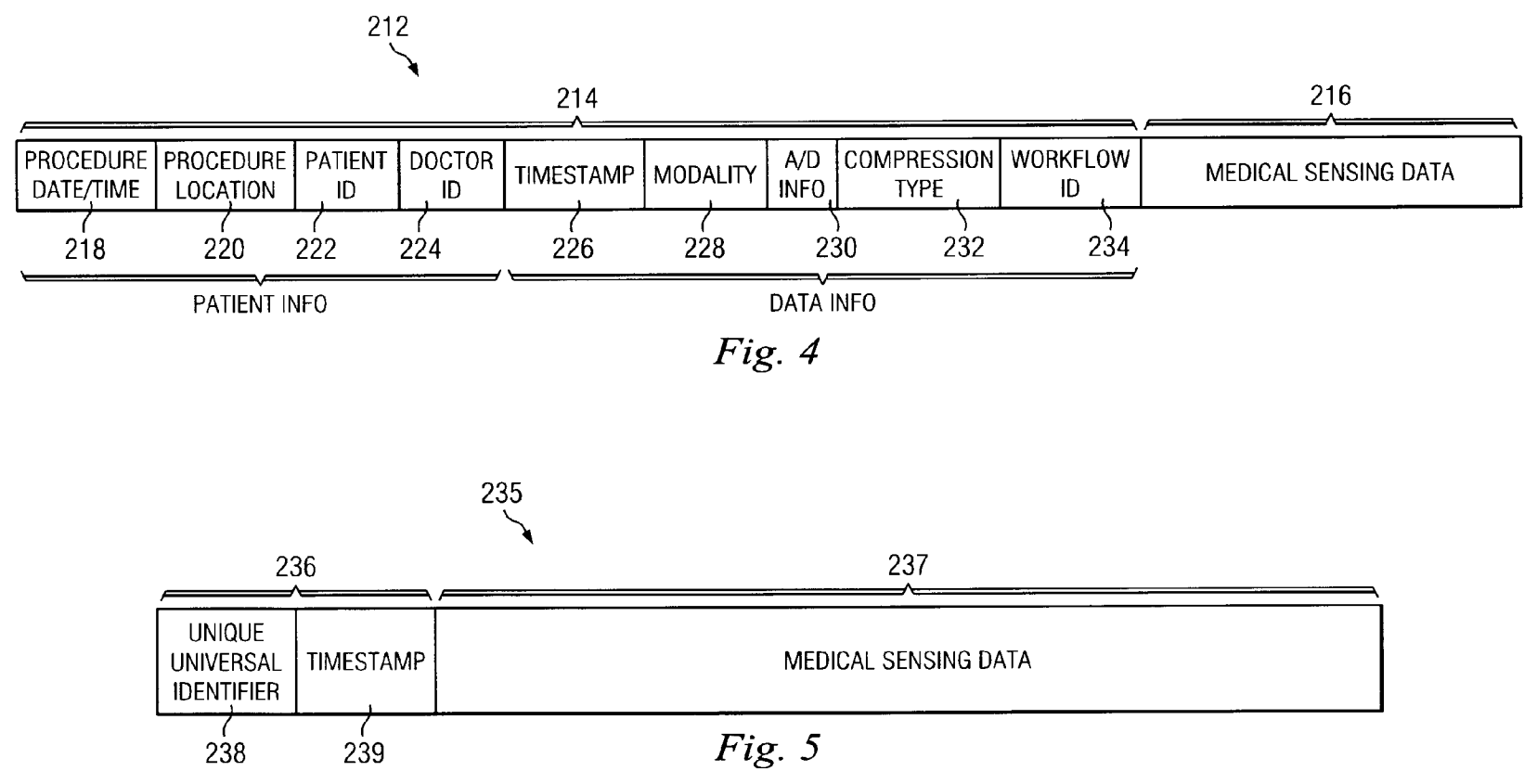

With reference now to FIG. 4, illustrated is a message format utilized by the distributed medical sensing system 100 in one embodiment of the present disclosure. As mentioned above, in some embodiments, a BUB may convert incoming medical sensing data into a plurality of messages containing digitized sensing data and associated identifying information. FIG. 4 illustrates an example message 212. The message 212 includes a header 214 and a payload 216. The payload 216 includes digitized medical sensing data collected with the medical sensing devices in system 100. The header 214 includes information associated with the sensing data in the payload 216. In more detail, the header includes a patient info portion and a data info portion, where the former generally includes information about the patient and procedure from which the medical sensing data came and the latter generally includes information about the data characteristics. More specifically, in the illustrated embodiment, the patient info portion of header 214 includes blocks 218, 220, 222, and 224 that respectively contain procedure date and time, procedure location (e.g. health care facility, catheter lab, etc), patient identification (e.g. name, social security number, date of birth, etc), and doctor identification (e.g. name, license number, etc). In some embodiments, the patient info portion may additionally contain security access information that limits where or by whom the sensing data may be viewed. As illustrated, the data info portion of the header 214 includes blocks 226, 228, 230, 232, and 234 that respectively contain a timestamp, modality of the sensing data, analog to digital conversion information, compression info, and a workflow ID. In one embodiment, the timestamp in block 226 may correspond to the point in time the data in payload 216 was collected. This timestamp may be used to facilitate co-registration of the sensing data with data of a different modality. The modality information in block 228 may include the modality of the data in payload 216 (e.g. IVUS, OCT, etc) and, in some embodiments, may also include the information about the specific medical sensing device with which the data was taken. The A/D information in block 230 may include information pertaining to the manner in which the sensing data in payload 216 was digitized, for example, sampling rate information and error correction information. The compression information in block 232 may include a flag indicating whether the data in payload 216 is compressed and, if necessary, the type of compression with which it is compressed. Finally, the workflow identification in block 234 may identify the workflow in which the data in payload 216 was collected. In some embodiments, this information may enable the centralized computer 180 to determine which processing application should process the data in payload 216. And it may enable a control surface in a catheter lab to determine which UI application should display the data once it is processed. The example message 212 is only one embodiment of a message that may be utilized in system 100, and, in other embodiments, the system 100 may utilize a different message format that includes additional and/or different information.

Further, in some embodiments, when a BUB first establishes a data connection with the centralized computer 180 to send medical sensing data, it may initially send one or more messages containing information similar to message 212. But, after the data connection has been established, the BUB may send messages with a smaller header containing only essential information such as a connection identifier and a timestamp. In such a scenario, the centralized computer 180 may store the remainder of the header info and associate it with the connection identifier. In this manner, medical sensing data may be more efficiently transmitted over the network-based system 100. The shortened message 236 is only one embodiment of a message that may be utilized in system 100, and, in other embodiments, the system 100 may utilize a different shortened message format that includes additional and/or different information. Or, the system 100 may not use a shortened message format at all.

With reference now to FIG. 5, illustrated is a different message format utilized by the distributed medical sensing system 100 in another embodiment of the present disclosure. FIG. 5 illustrates an example message 235. The message 235 includes a header 236 and a payload 237. Like the payload 216 of message 212, the payload 237 includes digitized medical sensing data collected with the medical sensing devices in system 100. However, the header 236 associates different information with the sensing data than the header 214 of message 212. The header 236 includes blocks 238 and 239 that respectively hold a unique universal identifier (UID) and a timestamp (or sequence number). Generally, the UID in block 238 is used to associate the data in payload 237 with data acquisition information stored in the centralized computer 180. In more detail, during the preparatory stages of a data acquisition workflow, the centralized computer 180 may allocate a UID and associate it with a storage location in the storage array 186 and a processing chain in the compute engine array 184. Further, the centralized computer 180 may push the UID down to the medical sensing tools that will be used in the procedure. Thus, when data acquisition starts, the BUB (or in some embodiments, the PIM) may tag the collected data with the UID by inserting it into the message header. In this manner, identifying information about the data such as patient identify, doctor identify, procedure date/time, location, data modality, data compression, PIM identify, catheter identify may be centrally stored on the centralized computer rather than stored in a message. Further, in some embodiments, the centralized computer 180 may allocate a different UID to associate with a processed version of medical sensing data. A network-connected user interface, such as bedside control surface 118, may then access the processed data using the associated UID. Still further, if one set of medical sensing data has multiple processed versions, each processed version may be associated with a different UID. In this manner, different user interfaces may specifically access different processed versions depending on the display capabilities of the user interface.

With reference now to FIGS. 1, 2, and 3, in operation, the distributed medical sensing system 100 is a distributed computational and storage solution for multiple modality medical sensing. Generally, in system 100, medical signaling and imaging data is collected by sensing instruments in catheter labs but processed and stored in a centralized, remote location and returned to the catheter labs for analysis by health care professionals.

For example, if the patient 114 is to undergo an IVUS procedure in catheter lab 102 a technician or doctor connects a phased-array catheter and associated PIM to the BUB 124 before the procedure. Upon connection, the bedside control surface 118 automatically displays the GUI associated with the IVUS procedure so a technician may start the IVUS workflow. As mentioned above, the centralized computer 180 may customize the IVUS workflow based on patient data retrieved from DICOM servers in the HIS 196. When the patient is ready, a health care provider inserts the sterile catheter into the patient's arteries and begins gathering tissue characteristic data. The PIM sends the data to the BUB 124 which, in turn, routes the data to the centralized computer 180 in the remote server room 182. In the centralized computer 180, an IVUS processing application in the application layer 210 interprets the tissue data and transforms it into IVUS image data. To decrease turn-around time, the software stack 208 may split up the workload and process the data in parallel using multiple compute engines in the array 184. After processing is complete, the processing application may store the image data in the storage array 186. The centralized computer 180 returns the processed image data to the control room 102 and the BUB 124 routes it to the bedside control surface 118 and the control room control surface 120. An IVUS UI application in the application layer 204 presents the image data to the user of the bedside control surface 118 as part of the IVUS workflow. At the same time, an IVUS UI application in the control room control surface 120 may present the processed diagnostic data in a different manner to a user of the control room control surface. The control room control surface 120 may also drive the image data to the boom display 122. In this manner, the health care professionals carrying out the IVUS procedure may simultaneously execute multiple tasks within the workflow, or simultaneously execute multiple workflows. For instance, a doctor manipulating the catheter may view a tomographic perspective of the procedure on the boom display 122 while a bedside technician controls the workflow from the bedside control surface 118 and a second technician in the control room 108 traces borders on the image data in real time using the control room control surface 120. In the case of the border tracing workflow, the centralized computer 180 may selectively provide the control room control surface 120 with IVUS image frames on which borders may be drawn. The control room control surface 120 may then send the centralized computer 180 the annotated IVUS images so that they may be archived. In this manner, a clinician operating the control room control surface may simultaneously and independently work on the medical sensing data being acquired in the adjacent catheter lab.

While the health care professionals perform the IVUS procedure in the catheter lab 102, the medical sensing system 100 may simultaneously support an OCT procedure in the catheter lab 104. In such a case, when the patient 170 is ready, a doctor connects an OCT catheter and associated PIM 160 to the BUB 168, the bedside control surface 162 presents the OCT workflow GUI, and the doctor begins collecting data. The BUB 168 routes the raw OCT data to the centralized computer 180 where an OCT processing application in the application layer 210 interprets the data. To process the OCT data efficiently, the software stack 208 assigns the data to compute engines not already processing data for the concurrent IVUS procedure. After the OCT image data has been processed, it is stored in the storage array 186 and returned to the BUB 168 in the catheter lab 104, where it is routed to the control surfaces 162 and 164. OCT UI applications executing in the application layers 204 present the image data to the doctor and technicians performing tasks in the OCT workflow.

Further, the medical sensing system 100 may simultaneously support a third procedure in catheter lab 106, such as an FFR procedure, in which FFR data is sent to centralized computer 180 for processing by an FFR processing application. Although FIG. 1 depicts only three catheter labs, one of ordinary skill in the art would recognize that the medical sensing system 100 may simultaneously support additional diagnostic procedure in additional catheter labs. Also, additional or different diagnostic procedure may be performed in the catheter labs 102, 104, and 106. For instance, three OCT procedures may be simultaneously performed in the catheter labs 102, 104, and 106, whereby the centralized computer 180 may process the OCT data from the labs in parallel using the compute engine array 184.

Additionally, multiple medical sensing modalities may be used concurrently in a single catheter lab. For instance, clinicians in catheter lab 102 may carryout a multimodality workflow that utilizes both IVUS and OCT imaging data. In such a case, a UI application on the bedside control surface 118 may coordinate the collection of data with two catheters. PIMs associated with the two catheters may be active and transmitting data to the centralized computer 180 where a co-registration processing application may interpret and co-register the image data. The co-registered data may then be returned to catheter lab 102 and a co-registration UI application may display synchronized images on the bedside control surface 118 and, if desired, boom display 122.

As mentioned above, the distributed medical sensing system 100 may include time synchronization elements to facilitate co-registration of data from different modalities. Temporal co-registration may be accomplished in different ways using system 100. First, time synchronization among devices in system 100 may be accomplished with network time synchronization using a network-based time synchronization protocol such as Precision Time Protocol (PTP) or Network Time Protocol (NTP). In such a case, the centralized computer 180 may act as a (grand)master clock where the BUBs in the system are the clients. In turn, the BUB may act as master time servers for sensing and control devices downstream of them in the catheter labs. Through this protocol, all medical sensing devices may be synchronized to within 100 μs or better. Data acquisition may then be controlled (i.e. started/stopped) at a pre-determined time by workflows executing on control surfaces. In this scenario, data is collected and time-stamped by each medical sensing device and forwarded through the system 100 to the centralized computer 180 for processing and archival. By having a timestamp based on a mutual clock, any sample from one data set may be matched temporally with a sample from another, even where the sample periods are not common and sampling clocks drift from the mutual network clock. As an example, in this embodiment, clinicians in catheter lab 102 may carry out a multimodality workflow by using a Forward-Looking Intracardiac Echo (FLICE) device and functional measurement pressure wires, where each is coupled to BUB 124 via their associated PIMs. In this case, BUB 124 is a local time server and each of these sensing devices is a time protocol client. After the catheters are positioned in the patient 114, the respective devices collect, timestamp, and forward data to the BUB 124, where it is forwarded to the centralized computer 180. A co-registration processing application in the application layer 210 reassembles the data into matched sets according to timestamps (i.e. matches FLICE frames to pressure samples) and sends the co-registered, processed data to the bedside control surface 118 for display. A UI application in the application layer 204 renders the pressure waves and moving FLICE images on the screen.

In other embodiments, rather than have the medical sensing devices themselves apply timestamps, the BUBs in system 100 may apply the timestamp at receipt of the sensing data before forwarding it on to the centralized computer for processing. In this manner, it is possible to get time-stamped data without requiring the medical sensing devices to act as a time protocol client. This is advantageous for legacy devices, third-party devices without network time protocol support, and devices that only transmit analog data to the BUBs. Further, in other embodiments, the centralized computer 180 may timestamp data as it arrives from medical sensing devices on the system 100.

Second, time synchronization among devices in medical sensing system 100 may be accomplished with real-time clocks driving synchronized sampling by medical sensing devices. As mentioned above, in some embodiments, the BUBs may include a dedicated real-time clock. In this scenario, synchronization signals from this clock may be distributed to the medical sensing devices coupled to the BUB and also a co-registration processor (e.g. the controller 138 in BUB 124 or the centralized computer 180). The synchronization signal may be carried by an individual conductor from the BUBs to the medical sensing devices or may be bundled into a system cable that carries network signals and power to the sensing devices. This synchronization signal may be a traditional, square-wave clock signal or a periodic, edge-based synch signal. In either case, the signal may be divided down or used as-is to produce a synchronization event on all sensing devices with a period less than or equal to the desired synchronization accuracy. A timestamp consisting of the enumerated counts of synchronization events may then be applied to collected data by each of the BUB-connected devices to identify a particular instant in time on a common time-base.

Figure 6:
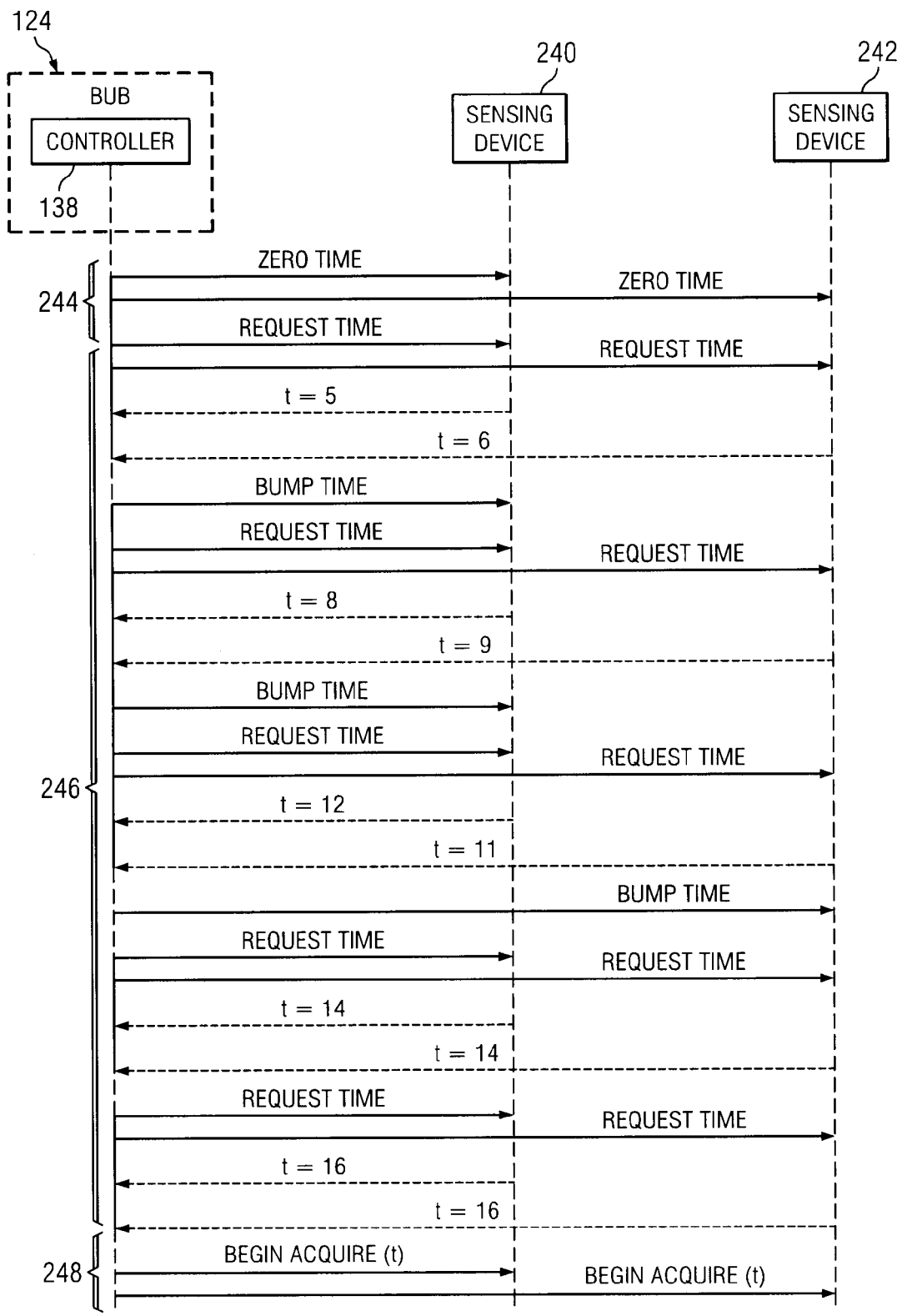
FIG. 6 is an illustration of a method for synchronizing data acquisition from multiple medical sensing devices in the system of FIG. 1.

With reference now to FIG. 6, illustrated is a method for synchronizing data acquisition from multiple medical sensing devices coupled to the BUB 124. Specifically, FIG. 6 illustrates time synchronization in an embodiment in which the controller 138 in BUB 124 acts as a co-registration processor for medical sensing devices 240 and 242 coupled to the BUB 124. In this embodiment, the BUB 124 includes a real-time clock that sends a synchronization signal to both the controller 138 and the sensing devices 240 and 242. During a initialization phase 244, the controller 138 oversees the setup of network connections to the medical sensing devices 240 and 242 connected to the BUB 124 and ensures they are in a state to begin synchronous data acquisition. Specifically, during the initialization phase 244, the controller 138 initially sends network messages to zero each sensing device's timestamp. Then, during a synchronization phase 246, the controller 133 requests timestamps from each device a number of times in synchronization with the synch signal until the sensing devices 240 and 242 are consistently reporting the same timestamp. If a timestamp received from one device is behind another (due to network congestion when sending the zero command or the request time command), the controller 138 will command the slower device to advance its timestamp by the difference between the two timestamps. This process is repeated until sensing devices 240 and 242 consistently report the same timestamp. At that time, a common time-base is established. In embodiments using a broadcast-capable network, the need to adjust timestamps on any sensing device may seldom be seen. Next, during a data acquisition phase 248 and after a common timestamp has been established between sensing devices 240 and 242, controller 138 sends a message to start synchronized data acquisition at a common time in the future. This start time is chosen to allow enough time for each sensing device to prepare for full data-rate acquisition in synchronization with the real-time clock. When the start time arrives, the sensing devices 240 and 242 begin collecting, time-stamping, and forwarding data to the controller 138.

Third, time synchronization among sensing devices in medical sensing system 100 may be accomplished with the use of a synchronous network such as SONET. As mentioned above, in some embodiments, the centralized computer 180 may communicate with the BUBs using the SONET protocol, and the BUBs, in turn, may communicate with the medical sensing devices coupled to them using SONET. In such a scenario, time-division multiplexing (TDM) is used to synchronize data sent from the BUBs to the centralized computer 180. For example, if two sensing devices are coupled to BUB 124, the communication channel from the BUB 124 to the centralized computer 180 may be divided into timeslots, where data from each sensing device is assigned one or more timeslots. If one of the sensing devices generates more data than the other per unit time (e.g. FFR vs. OCT), the data-heavy device may be dynamically assigned a greater number of timeslots. In any case, the medical sensing devices are each connected to the BUB 124 over a synchronous link with a throughput that is a divisor of the throughput of the communication interconnect 188 from the BUB 124 to the centralized computer 180. Based on clinician input and known medical sensing device characteristics (possibly determined dynamically), the BUB 124 may allocate timeslots to each device according to the workflow in the catheter lab 102. The BUB 124 may relay this timeslot configuration to the centralized computer, where it may be stored for future reference. After the medical sensing devices have been assigned timeslots as above, the devices begin streaming data to the BUB 124. At the co-registration begin time (a user-defined "start" point, or occurrence of some other identified condition), each TDM packet and all sub-channels of those packets, are assigned a monotonically increasing timestamp based on the packet number, packet size, number of channels configured in the timeslot map, and communication interconnect 188 bandwidth. Synchronized timestamps may then be applied to the data by the BUB 124 or the centralized computer 180.

Additionally, in some embodiments, the distributed medical sensing system 100 may be used to temporally co-register data acquired at substantially different times. In such embodiments, the centralized computer 180 may rely on a highly accurate time server which retains its frequency with high precision over long periods of time. Internet time servers using atomic clocks as master clocks commonly provide this functionality. The centralized computer 180 may alternatively have its own atomic clock in the system 100. In general, to co-register data sets acquired at different times, the timestamp of the first sample of each data set is subtracted from each sample, leaving only a delta time between samples. The two data sets may then be treated as if they were acquired simultaneously. For example, in one embodiment, OCT data may first be collected from the patient 114 in catheter lab 102, processed by centralized computer 180, and stored in data store array 186. Then, at a later time, IVUS data may be collected from the patient 114, processed by centralized computer 180, and stored in data store array 186. In each case, the data may be time-stamped using one of the above described methods. In another embodiment, this common frequency-controlled clock may be used to co-register sensing data from two sequential acquisitions during the same procedure. For example, the common clock may be used to co-register data from a pre-stent IVUS pullback and data from a post-stent IVUS pullback.

To co-register the collected and time-stamped OCT and IVUS data, a co-registration processing application in the application layer 210 on the centralized computer 180 may retrieve the data sets from the data store array 186 and subtract the first timestamp of each data set from all other timestamps in the sets. The co-registration processing application, through interaction with a clinician via a UI application on the bedside controller 118 or through an automatic location detection algorithm, chooses a data frame in each of the data sets that correspond to the same physical location in patient 114. The timestamps of these two frames are then subtracted, which gives an offset of timestamps between the data sets. Finally, this offset is subtracted from all timestamps in the data set with the greater value at the matched frame, so that the timestamps corresponding to the matched frames in each stack are equal. Additionally, in other embodiments, a similar method may be utilized to co-register archived data with data collected in real-time.

Further, the network-centric design of the distributed medical sensing system 100 may be advantageously utilized to perform any number of "telemedicine" tasks. For example, medical sensing data collected in catheter lab 102 and processed by the centralized computer 180 may be accessed by any number of network-connected devices outside of catheter lab 102 for training purposes, consultation purposes, etc. In addition to enabling remote, non-interactive viewing, the system 100 may provide remote interactive access to ongoing workflows. For instance, a consulting doctor in a remote health care facility may monitor a catheterization procedure and take control of the workflow if the need arises. In another example, a clinician performing an IVUS procedure in catheter lab 102 may request that a clinician performing a different procedure in catheter lab 104 momentarily take control of the IVUS workflow or ask for a second opinion of an IVUS image returned by the centralized computer 180. In such a case, the centralized computer 180 would direct the boom display 166 and control surface 162 in catheter lab 104 to temporarily display the IVUS workflow from catheter lab 102. Interactivity may be further expanded such that an entire workflow may be controlled by a network-connected clinician outside of the catheter lab. For example, robotic data collection tools may be connected to the system 100 through a BUB or other networked device. In such a scenario, the system 100 may provide remote control functionality to a remote clinician through a graphical user interface with appropriate robot-centric controls.

Figure 7:
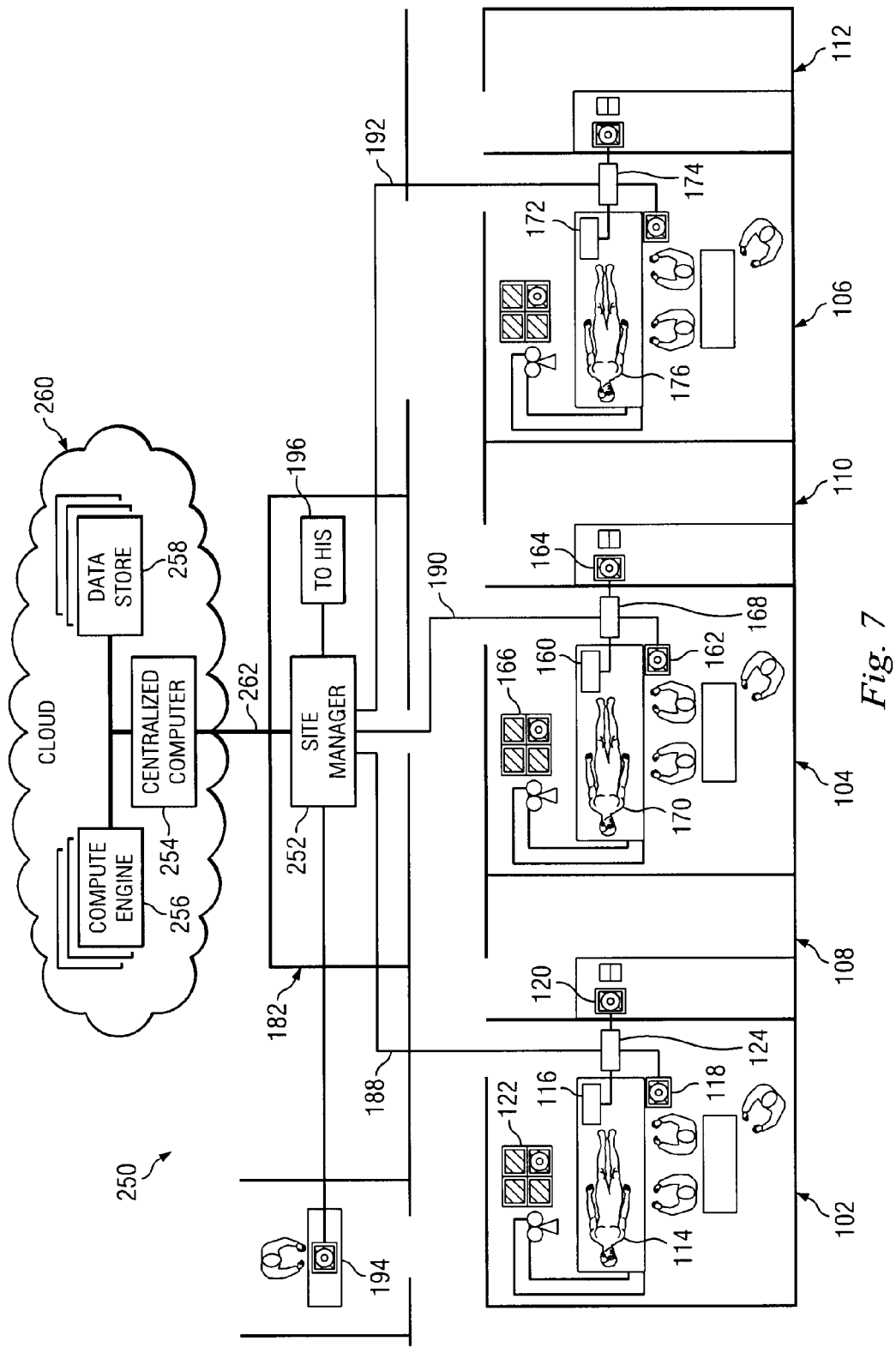
FIG. 7 is a schematic drawing depicting a distributed medical sensing system according to another embodiment of the present disclosure.

Referring now to FIG. 7, shown is a schematic drawing depicting a distributed medical sensing system 250 according to another embodiment of the present disclosure. The medical sensing system 250 is similar to the medical sensing system 100 shown in FIG. 1 and may be alternatively implemented in the health care facility with the catheter labs 102, 104, and 106. Like medical sensing system 100, medical sensing system 250 utilizes centralized computing and storage to support diagnostic procedures in the catheter labs, however, in system 250 the computing and storage resources are located off-site (i.e. in the "cloud").

In more detail, the medical sensing system 250 includes a site manager 252 stored in the centrally located server room 182. In an exemplary embodiment, the site manager 252 is a computer communicatively coupled to the BUBs 124, 168, and 174 via the communication interconnects 188, 190, and 192 and is operable to coordinate use of cloud resources and remote management. More specifically, the site manager 252 is operable to schedule data processing jobs for the medical sensing workflows in the catheter labs 102, 104, and 106. To mitigate against slower or un-reliable cloud networks, the site manager 252 may be configured to temporarily store data acquired locally before forwarding the data to the centralized computer 254. When the site manager 252 receives acknowledgement of successful storage of the data in the storage array 258 and/or receipt of processed data from the compute engine 256, the site manager may then safely discard the temporary local copy of the data. Further, in some embodiments, the site manager 252 may be configured to encrypt the unprocessed diagnostic data according to DICOM standards before sending it offsite for processing.

The medical sensing system 250 further includes a centralized computer 254, an array of compute engines 256, and a storage array 258, all stored in an off-site processing center 260. The off-site processing center 260 may be remote from the health care facility, in that it may be located in different city, state, or country. The centralized computer 254, array of compute engines 256, and storage array 258 are scalable to meet the needs of the processing center 260 and may be similar to the centralized computer 180, array of compute engines 184, and storage array 186 of FIG. 1. The computing resources in processing center 260 may be generally more powerful than those depicted in FIG. 1 because processing center 260 may serve the processing needs of many health care facilities. Like the centralized computer 180, the centralized computer 254 includes a software framework with a software stack similar to software stack 208 and a processing application layer similar to application layer 210. The processing application layer in centralized computer 254 thus includes processing applications corresponding to the types of medical sensing modalities performed at the health care facilities serviced by the processing center, and also may include co-registration processing applications used by the health care facilities. In some embodiments, the processing center 260 may be managed independently of the health care facilities it services and health care facilities may be charged for the use of the processing center. In one embodiment, health care facilities may be charged per procedure for the use of the computing resources in the processing center 260.

The centralized computer 254 in the processing center 260 is communicatively coupled to the site manager 252 via a communication interconnect 262. The communication interconnect 256 is a long-distance broadband connection operable to quickly transfer large datasets from the health care facility to the processing center 260 and back. In one embodiment, the communication interconnect 256 may be a 10 Gigabit Ethernet link or, but in other embodiments it may be another type of long distance broadband connection such as an ATM over SONET (OC-12 or better) link.

Although illustrative embodiments have been shown and described, a wide range of modification, change, and substitution is contemplated in the foregoing disclosure and in some instances, some features of the present disclosure may be employed without a corresponding use of the other features. For example, in some embodiments, the centralized computing resources of the medical sensing system 100 may be used to process non-cardiovascular diagnostic data such data from cranial or peripheral arteries, as well as data from non-vascular body portions. Further, the system 100 may be used to collect and process MRI data, or may be utilized in computer assisted surgery (CAS) applications. It is understood that such variations may be made in the foregoing without departing from the scope of the present disclosure. Accordingly, it is appropriate that the appended claims be construed broadly and in a manner consistent with the scope of the present disclosure.

What is claimed is:

1. A method of communicating medical sensing data, comprising:
    receiving, at a unit of a patient communication system within a sterile field, intravascular medical sensing data collected by an intravascular medical sensing device during an intravascular medical sensing procedure, the unit being communicatively coupled to a bedside controller disposed within the sterile field, wherein the bedside controller includes an integrated touchscreen display and is configured to control the intravascular medical sensing device to collect the intravascular medical sensing data in response to user input received on the integrated touchscreen display, and wherein the intravascular medical sensing data includes intravascular imaging data and wherein the intravascular medical sensing device is at least one of an intravascular ultrasound (IVUS) device and an optical coherence tomography (OCT) device;
    creating, with the unit of the patient communication system within the sterile field, a data message, the data message including
        at least a portion of the intravascular medical sensing data,
        information about the medical sensing procedure including a date and a time of the medical sensing procedure, a location of the medical sensing procedure, identification information about a patient undergoing the medical sensing procedure, identification information about the health care practitioner performing the medical sensing procedure, and security access information restricting the location at which the intravascular medical sensing data is accessible or the persons to whom the intravascular medical sensing data is accessible, and
        information about the intravascular medical sensing data including a timestamp generated by the unit of the patient communication system, modality information indicating if the medical sensing device is an IVUS device and an OCT device, analog to digital conversion information, compression information, and workflow information associated with the medical sensing procedure,
        wherein creating the data message includes creating a plurality of packets that together include all portions of the intravascular medical sensing data, wherein a first packet of the plurality of packets contains the at least a portion of the intravascular medical sensing data, the information about the medical sensing procedure, and the information about the intravascular medical sensing data, and wherein subsequent packets of the plurality of packets contain the at least a portion of the intravascular medical sensing data and a unique universal identifier associated with the medical sensing procedure, the subsequent packets omitting the information about the medical sensing procedure and the information about the intravascular medical sensing data;
    transmitting, with the unit of the patient communication system within the sterile field, the data message to a centralized computing device outside of the sterile field over a data network, wherein the transmitting includes transmitting the plurality of packets to the centralized computing device;
    processing, at the centralized computing device, the intravascular medical sensing data from the data message, the centralized computing device including a plurality of compute engines for simultaneously processing the intravascular medical sensing data; and
    outputting to the integrated touchscreen display of the bedside controller real-time intravascular images based on the processed intravascular medical sensing data.

2. The method of communicating medical sensing data of claim 1, including, with the unit of the patient communication system, digitizing the intravascular medical sensing data if it is received in analog form.

3. The method of communicating medical sensing data of claim 1, further including:
 receiving, at the unit of the patient communication system, a further data message including the intravascular medical sensing data in processed form from the centralized computing device over the data network; and
 transmitting the further data message to the integrated touchscreen display of the bedside controller to display the real-time intravascular images based on the processed intravascular medical sensing data.

4. A distributed medical sensing system, comprising:
 a computer communication network;
 a first patient communication system communicatively coupled to a first intravascular medical sensor device and the computer communication network, the first patient communication system including a first unit in a first sterile field that is operable to transmit, over the computer communication network, a first plurality of packets containing first intravascular medical data collected from a first patient by the first intravascular medical sensor device, the first unit being communicatively coupled to a first bedside controller disposed within the first sterile field, wherein the first bedside controller includes an integrated touchscreen display and is configured to control the first intravascular medical sensor device to collect the first intravascular medical data in response to user input received on the integrated touchscreen display, wherein the first intravascular medical data includes first intravascular imaging data and wherein the first intravascular medical sensor device is at least one of an intravascular ultrasound (IVUS) device and an optical coherence tomography (OCT) device;
 a second patient communication system communicatively coupled to a second intravascular medical sensor device and the computer communication network, the second patient communication system including a second unit in a second sterile field that is operable to send over the computer communication network a second plurality of packets containing second intravascular medical data collected from a second patient by the second intravascular medical sensor device, the second unit being communicatively coupled to a second bedside controller disposed within the second sterile field, wherein the second bedside controller includes an integrated touchscreen display and is configured to control the second intravascular medical sensor device to collect the second intravascular medical data in response to user input received on the integrated touchscreen display, wherein the second intravascular medical data includes second intravascular imaging data and wherein the second intravascular medical sensor device is at least one of an intravascular ultrasound (IVUS) device and an optical coherence tomography (OCT) device; and
 a centralized computing device including a plurality of compute engines for concurrently processing the first and second intravascular medical data, the centralized computing device positioned outside of the first and second sterile fields and communicatively coupled to the computer communication network and operable to:
  receive first and second plurality of packets;
  respectively process the first intravascular medical data based on the first patient information and process the second intravascular medical data based on the second patient information; and
  respectively output, to the integrated touchscreen display of the first bedside controller, real-time intravascular images based on the processed first intravascular medical data and output, to the integrated touchscreen display of the second bedside controller, real-time intravascular images based on the processed second intravascular medical data;
 wherein the first and second plurality of packets respectively further include
  information about a medical sensing procedure including a date and a time of the medical sensing procedure, a location of the medical sensing procedure, identification information about a patient undergoing the medical sensing procedure, identification information about the health care practitioner performing the medical sensing procedure, and security access information restricting the location at which the intravascular medical sensing data is accessible or the persons to whom the intravascular medical sensing data is accessible, and
  information about the intravascular medical data including a timestamp generated by the unit of the patient communication system, modality information indicating if the intravascular medical sensor device is an IVUS device and an OCT device, and workflow information associated with the medical sensing procedure; and
 wherein a first packet of the first and second plurality of packets respectively contains the first and second intravascular medical data, the information about the medical sensing procedure, and the information about the medical sensing data, and wherein subsequent packets of the plurality of packets respectively contain the first and second intravascular medical data and a unique universal identifier associated with the medical sensing procedure, the subsequent packets omitting the information about the medical sensing procedure and the information about the intravascular medical data.

5. The distributed medical sensing system of claim 4, wherein the first and second intravascular medical data are associated with the same medical sensing modality.

6. The distributed medical sensing system of claim 4, wherein the first and second intravascular medical data are associated with different medical sensing modalities.

7. The distributed medical sensing system of claim 6, wherein the centralized computing device is further operable to process the first intravascular medical data with a first processing application associated with the first modality and further operable to process the second intravascular medical data with a second processing application associated with the second modality.

8. The distributed medical sensing system of claim 4, wherein the centralized computing device is further operable to process the first intravascular medical data with a first processing application associated with the first modality, the first processing application being one of a plurality of processing applications executable by the centralized computing device.

9. The distributed medical sensing system of claim 4, wherein the first patient communication system includes an analog to digital converter operable to digitize the first intravascular medical data and a communication module communicatively coupled to the computer communication network.

10. The distributed medical sensing system of claim 4, wherein the first unit of the first patient communication system is a first bedside utility box (BUB) disposed within a first procedure room and the second unit of the second patient communication system is a second BUB disposed within a second procedure room different than the first procedure room.

11. The distributed medical sensing system of claim 4, wherein the first unit of the first patient communication system is a patient isolation module (PIM).

12. The distributed medical sensing system of claim 4, wherein the first unit of the first patient communication system is operable to compress the first intravascular medical data before sending the first plurality of packets over the computer communication network.

13. A method of processing medical data, comprising:
receiving, at a centralized computing device, first message data over a computer communication network, the first message data including
first intravascular medical sensing data generated by a first intravascular medical sensor device during a first medical sensing procedure, wherein the first intravascular medical sensing data includes first intravascular imaging data and wherein the first intravascular medical sensor device is at least one of an intravascular ultrasound (IVUS) device and an optical coherence tomography (OCT) device,
information about the first medical sensing procedure including a date and a time of the medical sensing procedure, a location of the medical sensing procedure, identification information about a patient undergoing the medical sensing procedure, identification information about the health care practitioner performing the medical sensing procedure, and security access information restricting the location at which the intravascular medical sensing data is accessible or the persons to whom the intravascular medical sensing data is accessible, and
information about the first intravascular medical sensing data including a timestamp generated by the unit of the patient communication system, modality information indicating if the first intravascular medical sensor device is an IVUS device and an OCT device, and workflow information associated with the medical sensing procedure,
wherein the data message includes a plurality of packets, the first packet of the plurality of packets containing the intravascular medical sensing data, the information about the medical sensing procedure, and the information about the medical sensing data, and subsequent packets of the plurality of packets containing the intravascular medical sensing data and a unique universal identifier associated with the medical sensing procedure, wherein the subsequent packets omit the information about the medical sensing procedure and the information about the medical sensing data;
processing, with the centralized computing device, the first intravascular medical sensing data based on the information about the first medical sensing procedure and the information about the first intravascular medical sensing data, the centralized computing device including a plurality of compute engines for simultaneously processing the intravascular medical sensing data; and
transmitting, with the centralized computing device, second message data to a first bedside controller over the computer communication network, the first bedside controller including a touchscreen display component and configured to control the first intravascular medical sensor device to acquire the first intravascular medical sensing data in response to user input received on the touchscreen display component, the second message data containing the first intravascular medical sensing data in processed form, the touchscreen display component of the first bedside controller being operable to display real-time intravascular images based on the first intravascular medical sensing data in processed form.

14. The method of processing medical data of claim 13, including receiving, at the centralized computing device and concurrently with the receiving the first message data, third message data over the computer communication network, the third message data including second intravascular medical sensing data generated by a second intravascular medical sensor device during a second medical sensing procedure, information about the second medical sensing procedure, and information about the second intravascular medical sensing data, wherein the second intravascular medical data includes second intravascular imaging data and wherein the second intravascular medical sensor device is at least one of an intravascular ultrasound (IVUS) device and an optical coherence tomography (OCT) device.

15. The method of processing medical data of claim 14, including processing, with the centralized computing device and concurrently with the processing the first intravascular medical data, the second intravascular medical data based on the information about the second medical sensing procedure and the information about the second intravascular medical sensing data.

16. The method of processing medical data of claim 14, wherein the first and second intravascular medical data are associated with the same medical sensing modality.

17. The method of processing medical data of claim 13, wherein the processing includes processing the first intravascular medical data with a first processing application associated with a medical sensing modality of the first intravascular medical data, the first processing application being one of a plurality of processing applications executable by the centralized computing device.

18. The method of processing medical data of claim 13, wherein the processing the first intravascular medical data includes transforming the first intravascular medical data into image data representative of the first intravascular medical data.

* * * * *